United States Patent
Yamamoto et al.

(10) Patent No.: US 9,394,226 B2
(45) Date of Patent: Jul. 19, 2016

(54) 3,4-DIALKYLBIPHENYLDICARBOXYLIC ACID COMPOUND, 3,4-DICARBOALKOXYBIPHENYL-3',4'-DICARBOXYLIC ACID AND CORRESPONDING ACID ANHYDRIDES, AND PROCESSES FOR PRODUCING THESE COMPOUNDS

(71) Applicant: Ube Industries, Ltd., Ube-shi (JP)

(72) Inventors: Yasushi Yamamoto, Ube (JP); Yasutaka Yoshida, Ube (JP); Hikaru Yatabe, Ube (JP); Yoshihiro Yamauchi, Ube (JP); Tetsurou Tsuji, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 14/503,908

(22) Filed: Oct. 1, 2014

(65) Prior Publication Data

US 2015/0025263 A1    Jan. 22, 2015

Related U.S. Application Data

(62) Division of application No. 13/878,133, filed as application No. PCT/JP2011/073265 on Oct. 7, 2011, now Pat. No. 8,859,801.

(30) Foreign Application Priority Data

Oct. 8, 2010 (JP) .................................. 2010-228108
Jan. 26, 2011 (JP) .................................. 2011-014419

(51) Int. Cl.

| C07C 67/00 | (2006.01) |
|---|---|
| C07C 67/30 | (2006.01) |
| C07C 67/313 | (2006.01) |
| C07C 67/317 | (2006.01) |
| C07C 67/343 | (2006.01) |
| C07C 69/76 | (2006.01) |
| C07C 69/78 | (2006.01) |

(52) U.S. Cl.
CPC ............... *C07C 67/30* (2013.01); *C07C 67/313* (2013.01); *C07C 67/317* (2013.01); *C07C 67/343* (2013.01); *C07C 69/76* (2013.01); *C07C 69/78* (2013.01); *C07C 2101/14* (2013.01)

(58) Field of Classification Search
CPC ..... C07C 69/76; C07C 67/343; C07C 67/313; C07C 67/317; C07C 69/753; C07C 2101/14; C07C 67/30; C07C 69/78
See application file for complete search history.

(56) References Cited

U.S. PATENT DOCUMENTS

| 3,726,914 A | 4/1973 | Engenbrecht et al. |
| 6,509,507 B2 * | 1/2003 | Spreitzer ................. C07B 37/04 428/917 |
| 8,859,801 B2 * | 10/2014 | Yamamoto ............ C07C 67/313 560/77 |

FOREIGN PATENT DOCUMENTS

| JP | A-S48-54048 | 7/1973 |
| JP | A-S55-141417 | 11/1980 |
| JP | A-S61-106541 | 5/1986 |
| JP | A-S62-026238 | 2/1987 |
| JP | A-H02-115143 | 4/1990 |
| JP | B-H05-3857 | 1/1993 |
| JP | A-2006-151946 | 6/2006 |

OTHER PUBLICATIONS

International Preliminary Report on Patentability issued on May 8, 2013 for International Application No. PCT/JP2011/073265.

\* cited by examiner

*Primary Examiner* — Yevegeny Valenrod
*Assistant Examiner* — Blaine G Doletski
(74) *Attorney, Agent, or Firm* — Knobbe Martens Olson & Bear LLP

(57) ABSTRACT

3,4-Dicarboalkoxybiphenyl-3',4'-dicarboxylic acid represented by the general formula (1):

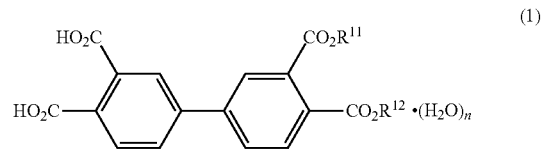

in which $R^{11}$ and $R^{12}$ each represents an alkyl group having 1 to 4 carbon atoms, and n represents the number of waters of hydration that is 0 or 1, and the corresponding anhydride.

2 Claims, No Drawings

3,4-DIALKYLBIPHENYLDICARBOXYLIC ACID COMPOUND, 3,4-DICARBOALKOXYBIPHENYL-3',4'-DICARBOXYLIC ACID AND CORRESPONDING ACID ANHYDRIDES, AND PROCESSES FOR PRODUCING THESE COMPOUNDS

RELATED APPLICATIONS

This application is a divisional of U.S. patent application Ser. No. 13/878,133, filed Apr. 5, 2013, which is the U.S. National Phase under 35 U.S.C. §371 of International Application No. PCT/JP2011/073265, filed Oct. 7, 2011, designating the U.S., and published in Japanese as WO 2012/046857 on Apr. 12, 2012, which claims priority to Japanese Patent Application No. 2010-228108 filed Oct. 8, 2010; and Japanese Patent Application No. 2011-014419, filed Jan. 26, 2011. The entire content of these applications is incorporated herein by reference.

TECHNICAL FIELD

The present invention relates to novel compounds, a 3,4-dialkylbiphenyldicarboxylic acid compound and a 3,4-dicarboalkoxybiphenyl-3',4'-dicarboxylic acid (including the corresponding acid anhydride), and methods for producing these compounds.

BACKGROUND ART

Many publications disclose biphenyltetracarboxylic acid and an acid anhydride thereof used as a raw material for the production of polyimides, and a method for producing the same (Patent Literatures 1 to 4, etc.). For example, as a method for producing 3,4,3',4'-biphenyltetracarboxylic acid and an acid anhydride thereof, Patent Literature 3 describes a production method comprising dimerization of halogenated phthalic acids, and Patent Literature 4 describes a production method comprising oxidation of a methyl group of 3,4,3',4'-tetramethylbiphenyl.

CITATION LIST

Patent Literature

Patent Literature 1: Japanese Patent Laid-Open No. S61 (1986)-106541
Patent Literature 2: Japanese Patent Laid-Open No. S55 (1980)-141417
Patent Literature 3: Japanese Patent Publication No. H5(1993)-3857
Patent Literature 4: Japanese Patent Laid-Open No. S48 (1973)-54048

SUMMARY OF INVENTION

Means for Solving the Problems

The present invention provides novel compounds, a 3,4-dicarboalkoxybiphenyl-3',4'-dicarboxylic acid (including the corresponding acid anhydride) and a 3,4-dialkylbiphenyl-3', 4'-dicarboxylic acid compound, and methods for producing these compounds.

Specifically, the present invention relates to the following items.

1. A 3,4-Dicarboalkoxybiphenyl-3',4'-dicarboxylic acid (including the corresponding acid anhydride) represented by the general formula (1):

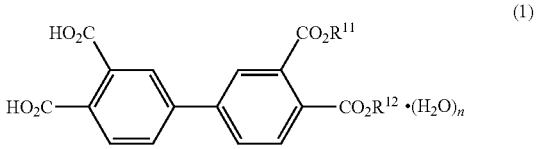

wherein $R^{11}$ and $R^{12}$ each represents an alkyl group having 1 to 4 carbon atoms, and n represents the number of waters of hydration that is 0 or 1.

2. A 3,4-dialkylbiphenyl-3',4'-dicarboxylic acid compound represented by the general formula (2):

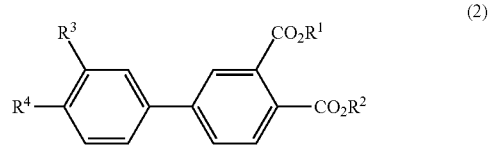

wherein $R^1$ and $R^2$ each represents a hydrogen atom or an alkyl group having 1 to 4 carbon atoms, and $R^3$ and $R^4$ each represents an alkyl group having 1 to 4 carbon atoms.

3. A 3,4-dimethylbiphenyldicarboxylic acid compound represented by the general formula (3):

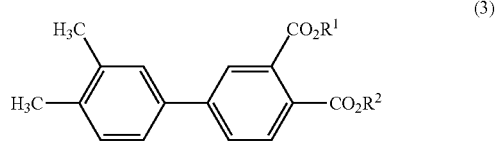

wherein $R^1$ and $R^2$ each represents a hydrogen atom or an alkyl group having 1 to 4 carbon atoms.

4. A method for producing the 3,4-dicarboalkoxybiphenyl-3', 4'-dicarboxylic acid (including the corresponding acid anhydride) represented by the general formula (1-1), wherein
the method comprises a step of oxidizing the 3,4-dialkylbiphenyl-3',4'-dicarboxylic acid compound represented by the general formula (2) or the 3,4-dimethylbiphenyldicarboxylic acid compound represented by the general formula (3) (hereinafter referred to as an "oxidation step"):

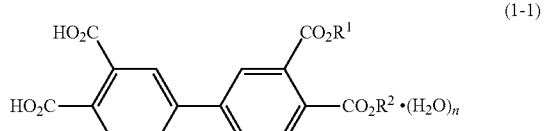

wherein $R^1$ and $R^2$ each represents a hydrogen atom or an alkyl group having 1 to 4 carbon atoms, and n represents the number of waters of hydration that is 0 or 1.

5. The production method according to 4 above, wherein, in the oxidation step, the oxidation is performed with molecular oxygen in the presence of a metallic compound and a pro-oxidant.

6. The production method according to 5 above, wherein the pro-oxidant is a bromide, a hydroxyimide compound, or a mixture thereof.
7. A method for producing the 3,4-dialkylbiphenyldicarboxylic acid compound represented by the general formula (2), wherein
the method comprises subjecting the 3,4-dicarboalkoxycyclohexyl-3',4'-alkylbenzene compound represented by the general formula (4-1) to a dehydrogenation reaction in the presence of a metallic catalyst:

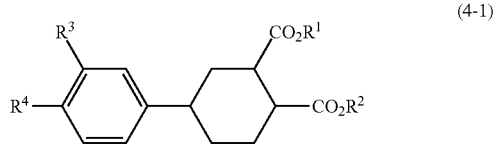

(4-1)

wherein $R^1$, $R^2$, $R^3$, and $R^4$ have the same definitions as those described above.
8. A method for producing the 3,4-dialkylbiphenyldicarboxylic acid compound represented by the general formula (2), wherein
the method comprises reacting a 4-halogenophthalic acid compound represented by the general formula (5) with the 3,4-dialkylphenyl boron compound represented by the general formula (6-1) in the presence of a base and a palladium catalyst:

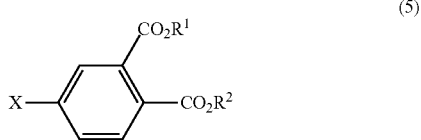

(5)

wherein $R^1$ and $R^2$ have the same definitions as those described above, and X represents a halogen atom, and

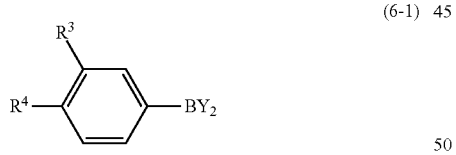

(6-1)

wherein $R^3$ and $R^4$ have the same definitions as those described above; and Y represents a hydroxyl group, or a linear or branched alkoxyl group having 1 to 6 carbon atoms which may be the same or different, wherein the carbon atoms of the alkoxyl groups may bind to one another to form a ring.
9. Use of the 3,4-dicarboalkoxybiphenyl-3',4'-dicarboxylic acid (including the corresponding acid anhydride) represented by the general formula (1) in the production of 3,4,3',4'-biphenyltetracarboxylic acid or an anhydride thereof.

Effect of the Invention

The 3,4-dicarboalkoxybiphenyl-3',4'-dicarboxylic acid (including the corresponding acid anhydride) and 3,4-dialkylbiphenyl-3',4'-dicarboxylic acid compound of the present invention are both novel compounds, and these are useful compounds that can be induced to a 3,4,3',4'-biphenyltetracarboxylic acid (hereinafter also referred to as s-BPTA) and an acid anhydride thereof (hereinafter also referred to as s-BPDA), which is used, for example, as raw materials for the production of polyimides. In addition, since the 3,4-dicarboalkoxybiphenyl-3',4'-dicarboxylic acid has two carboxyl groups, it can also be used as a polyimide foam, a terminal modifier, and the like.

EMBODIMENT FOR CARRYING OUT THE INVENTION

The 3,4-dicarboalkoxybiphenyl-3',4'-dicarboxylic acid (including the corresponding acid anhydride) of the present invention (hereinafter also referred to as compound (1)) is represented by the general formula (1) as shown below. The compound (1) is a novel compound.

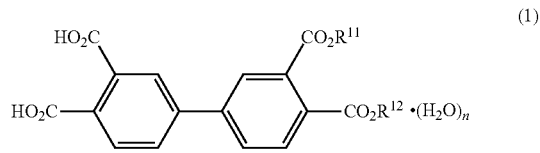

(1)

wherein $R^{11}$ and $R^{12}$ each represents an alkyl group having 1 to 4 carbon atoms, and n represents the number of waters of hydration that is 0 or 1.

The corresponding acid anhydride means a 3,4-dicarboalkoxybiphenyl-3',4'-dicarboxylic acid anhydride represented by the general formula (1'). This compound represented by the general formula (1') can be easily converted to a 3,4-dicarboalkoxybiphenyl-3',4'-dicarboxylic acid (compound (1)) by a general hydrolytic reaction.

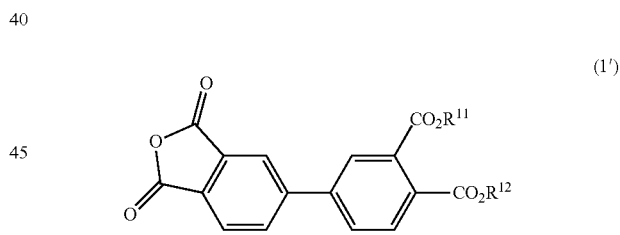

(1')

wherein $R^{11}$ and $R^{12}$ have the same definitions as those described above.

In the above general formulae (1) and (1'), $R^{11}$ and $R^{12}$ each represents an alkyl group having 1 to 4 carbon atoms, and preferably each represents a linear or branched alkyl group having 1 to 4 carbon atoms, such as a methyl group, an ethyl group, an n-propyl group, an isopropyl group, an n-butyl group, an isobutyl group, or a t-butyl group. $R^{11}$ and $R^{12}$ may be identical to or different from each other. Moreover, n represents the number of waters of hydration that is 0 or 1. That is to say, the 3,4-dicarboalkoxybiphenyl-3',4'-dicarboxylic acid may adopt either a form that does not contain water of hydration, or a form as a monohydrate.

The 3,4-dialkylbiphenyl-3',4'-dicarboxylic acid compound of the present invention (hereinafter also referred to as compound (2)) is represented by the general formula (2) as shown below. The compound (2) is a novel compound.

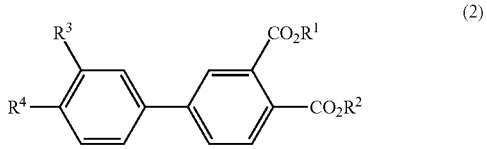

wherein $R^1$ and $R^2$ each represents a hydrogen atom or an alkyl group having 1 to 4 carbon atoms, and $R^3$ and $R^4$ each represents an alkyl group having 1 to 4 carbon atoms.

In the general formula (2), $R^1$ and $R^2$ each represents a hydrogen atom or an alkyl group having 1 to 4 carbon atoms, and preferably each represents a linear or branched alkyl group having 1 to 4 carbon atoms, such as a methyl group, an ethyl group, an n-propyl group, an isopropyl group, an n-butyl group, an isobutyl group, or a t-butyl group. $R^1$ and $R^2$ may be identical to or different from each other.

In the present invention, a preferred example of the compound (2) is a 3,4-dimethylbiphenyldicarboxylic acid compound represented by the general formula (3) (hereinafter also referred to as compound (3)), in which $R^3$ and $R^4$ each represents a methyl group.

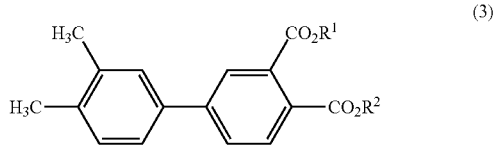

wherein $R^1$ and $R^2$ each represents a hydrogen atom or an alkyl group having 1 to 4 carbon atoms.

By a production method comprising a step of oxidizing the above described compound (2) or compound (3) (hereinafter, this step is also referred to as "oxidation step"), the 3,4-dicarboalkoxybiphenyl-3',4'-dicarboxylic acid (including the corresponding acid anhydride) represented by the following general formula (1-1) can be produced:

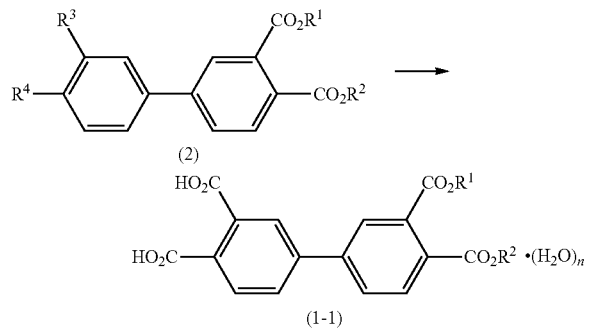

wherein $R^1$ and $R^2$ each represents a hydrogen atom or an alkyl group having 1 to 4 carbon atoms, $R^3$ and $R^4$ each represents an alkyl group having 1 to 4 carbon atoms, and n represents the number of waters of hydration that is 0 or 1. It is to be noted that, when the compound (1-1) is obtained in the form of a mixture of a compound in which n=0, and a compound in which n=1, there may be obtained an analysis result in which n would be a number between 0 and 1.

<Production Method of Compound (2) or (3)>

First, a method for producing the 3,4-dialkylbiphenyl-3', 4'-dicarboxylic acid compound (compound (2)) represented by the general formula (2) or the 3,4-dimethylbiphenyldicarboxylic acid compound (compound (3)) represented by the general formula (3) will be described. These compounds can be obtained by a synthetic method described in the following method (A) or (B).

[Method (A)]

In the method (A), a 3,4-dicarboalkoxycyclohexyl-3',4'-dialkylbenzene compound represented by the general formula (4-1) (hereinafter also referred to as compound (4-1)), or a 3,4-dicarboalkoxycyclohexyl-3',4'-dimethylbenzene compound represented by the general formula (4-2) (hereinafter also referred to as compound ((4-2)), is subjected to a dehydrogenation reaction in the presence of a metallic catalyst. In order to produce the compound (2), the compound (4-1) is used. In order to produce the compound (3), the compound (4-2) is used.

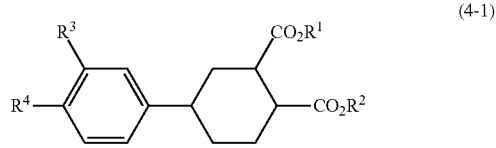

wherein $R^1$, $R^2$, $R^3$, and $R^4$ have the same definitions as those described above.

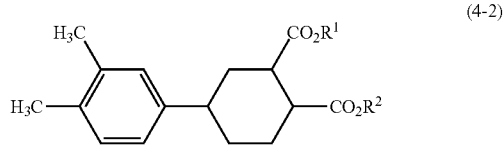

wherein $R^1$ and $R^2$ have the same definitions as those described above.

The 3,4-dicarboalkoxycyclohexyl-3',4'-dialkylbenzene compound represented by the above general formula (4-1) can be produced by reacting o-dialkylbenzene with a 3,4-dicarboalkoxycyclohexene in the presence of an alkylation reaction catalyst prepared by depositing a di- or more valent metallic ion on an inorganic structure having ion-exchange capacity.

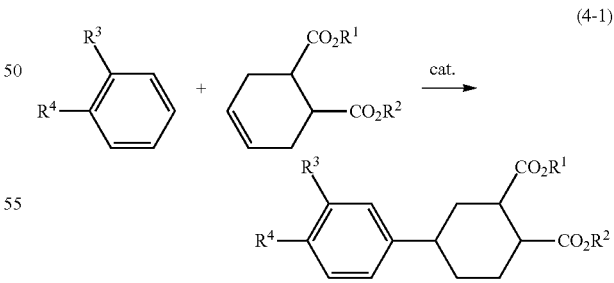

As a metallic catalyst used in the method (A) of the present invention, a catalyst carrier on which a metallic atom is deposited is preferably used, for example. Examples of the aforementioned metallic catalyst include metallic catalysts comprising at least one metallic atom selected from the group consisting of palladium, platinum, ruthenium, rhodium, iridium, iron, cobalt, nickel and copper. The type of the aforementioned catalyst support is not particularly limited, as long as it is able to deposit a metallic atom thereon. Examples of the catalyst support that can be preferably used herein include activated carbon, silica, alumina, silica-alumina, zeolite, and ion exchange resin. These metallic catalysts may be used singly or in combination of two or more types.

The above described metallic catalyst is used at preferably 0.1 wt % to 50 wt %, and more preferably 5 wt % to 20 wt %, based on the mass of the compound (4-1) or the compound (4-2).

In the method (A) of the present invention, the compound (4-1) or the compound (4-2) is mixed with a metallic catalyst, so that they are reacted under an inert gas atmosphere. The reaction temperature applied during the reaction is preferably 100° C. to 500° C., and more preferably 250° C. to 400° C. The reaction pressure is preferably 0.01 to 0.3 MPa, and more preferably 0.05 to 0.1 MPa. The reaction mode may be either a gaseous phase or a liquid phase, or a fixed bed or a fluidized bed. The reaction is preferably carried out as a fixed-bed flow-type reaction.

[Method (B)]

In the method (B), a 4-halogenophthalic acid compound represented by the general formula (5) (hereinafter also referred to as compound (5)) is reacted with a 3,4-dialkylphenyl boron compound represented by the general formula (6-1) (hereinafter also referred to as compound (6-1)) or a 3,4-dimethylphenyl boron compound represented by the general formula (6-2) (hereinafter also referred to as compound (6-2)) in the presence of a base and a palladium catalyst. In order to produce the compound (2), the compound (6-1) is used. In order to produce the compound (3), the compound (6-2) is used.

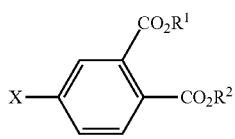
(5)

wherein $R^1$ and $R^2$ have the same definitions as those described above, and X represents a halogen atom.

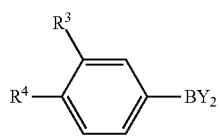
(6-1)

wherein $R^3$ and $R^4$ have the same definitions as those described above, and Y represents a hydroxyl group, or a linear or branched alkoxyl group having 1 to 6 carbon atoms which may be the same or different, wherein the carbon atoms of the alkoxyl groups may bind to one another to form a ring.

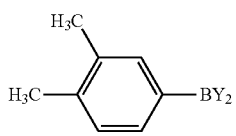
(6-2)

wherein Y represents a hydroxyl group, or a linear or branched alkoxyl group having 1 to 6 carbon atoms which may be the same or different, wherein the carbon atoms of the alkoxyl groups may bind to one another to form a ring.

In the general formula (5), X represents a halogen atom such as a fluorine atom, a chlorine atom, a bromine atom, or an iodine atom.

The above described 3,4-dialkylphenyl boron compound (compound (6-1)) or 3,4-dimethylphenyl boron compound (compound (6-2)) is used in an amount of preferably 1.0 to 1.5 moles, more preferably 1.01 to 1.3 moles, and particularly preferably 1.01 to 1.1 moles, based on 1 mole of the 4-halogenophthalic acid compound (compound (5)).

Examples of the base used in the method (B) of the present invention include: alkali metal hydroxides such as lithium hydroxide, sodium hydroxide, potassium hydroxide, magnesium hydroxide or calcium hydroxide; alkali metal carbonates such as lithium carbonate, sodium carbonate, sodium hydrogen carbonate, potassium carbonate, potassium hydrogen carbonate, magnesium carbonate, calcium carbonate, barium carbonate or cesium carbonate; alkali metal phosphates such as lithium phosphate, sodium phosphate or potassium phosphate; alkali metal acetates such as lithium acetate, sodium acetate, magnesium acetate or calcium acetate; alkali metal alkoxides such as lithium methoxide, lithium t-butoxide, sodium methoxide or sodium t-butoxide; and alkali metal halides such as cesium fluoride, sodium fluoride, potassium fluoride or calcium fluoride. These bases may be used singly or in combination of two or more types.

The above described base is used in an amount of preferably 0.1 to 10 moles, more preferably 0.5 to 5 moles, and particularly preferably 1 to 2 moles, based on 1 mole of the 4-halogenophthalic acid compound.

Examples of the palladium catalyst used in the method (B) of the present invention include palladium chloride, palladium acetate, tetrakis(triphenylphosphine)palladium, and dichlorobis(triphenylphosphine)palladium. The above described palladium catalyst may comprise late transition metals such as copper, nickel, platinum, rhodium, iridium or ruthenium. These palladium catalysts may be used singly or in combination of two or more types, and these palladium catalysts may previously be prepared in a reaction system and may be then used.

The above described palladium catalyst is used in an amount of preferably 0.001 to 0.15 moles, and more preferably 0.01 to 0.1 moles, based on 1 mole of the 4-halogenophthalic acid compound.

The reaction in the method (B) of the present invention is desirably carried out in the presence of a solvent. The type of a solvent used is not particularly limited, as long as it does not inhibit the reaction. Examples of such a solvent include: water; ethers such as diethyl ether, tetrahydrofuran, cyclopentyl methyl ether, t-butyl methyl ether, 1,4-dioxane or 1,2-dimethoxyethane; alcohols such as methanol, ethanol, isopropyl alcohol, t-butanol or t-amyl alcohol; aromatic hydrocarbons such as benzene, toluene, chlorobenzene or xylene; and halogenated aromatic hydrocarbons such as chlorobenzene. These solvents may be used singly or in combination of two or more types.

The above described solvent is used in an amount of preferably 0.1 to 10 L, and more preferably 1 to 5 L, based on 1 mole of the 4-halogenophthalic acid compound.

The method (B) of the present invention is carried out by mixing, for example, a 4-halogenophthalic acid compound, a 3,4-dialkylphenyl boron compound or a 3,4-dimethylphenyl boron compound, a base, a palladium catalyst, and a solvent, and then reacting these compounds while stirring them. The reaction temperature applied during the reaction is preferably 0° C. to 150° C., and more preferably 20° C. to 100° C. The reaction pressure is not particularly limited, and it is generally an atmospheric pressure.

After completion of the reaction, the 3,4-dialkylbiphenyldicarboxylic acid compound (compound (2)) or the 3,4-dimethylbiphenyldicarboxylic acid compound (compound (3)) obtained by the above described method (A) or method (B) is isolated and purified by a common method such as filtration, extraction, distillation, sublimation, recrystallization or column chromatography.

The thus obtained 3,4-dialkylbiphenyldicarboxylic acid compound or 3,4-dimethylbiphenyldicarboxylic acid compound can be induced to the 3,4-dicarboalkoxybiphenyl-3', 4'-dicarboxylic acid (including the corresponding acid anhydride) or the 3,4,3',4'-biphenyltetracarboxylic acid by oxidizing an alkyl group or methyl group thereof, as described later.

<Method for Producing Compound (1-1)>

Next, a method for producing a compound (1-1) using the compound represented by the general formula (2) or the general formula (3) will be described. As described above, the compound (1-1) can be obtained by a production method comprising an oxidation step of oxidizing the compound (2) or the compound (3). In this oxidation step, a method of oxidizing the compound (2) or the compound (3) with molecular oxygen in the presence of a metallic compound and a pro-oxidant is preferably applied.

The metallic compound used in the oxidation step of the present invention is a metallic compound containing at least one type of metal selected from the group consisting of cobalt, manganese, nickel, cerium, zirconium, vanadium, copper, molybdenum and iron. Preferably, a metallic compound containing at least one type of metal selected from the group consisting of cobalt, manganese and zirconium is used. Examples of the form of such a metallic compound include organic acid salts, halides, and carbonates. Preferably, acetate and bromide are used. These metallic compounds may be used singly or in combination of two or more types.

The above described metallic compound is used in an amount of preferably 0.001 to 0.2 moles, more preferably 0.005 to 0.1 moles, and particularly preferably 0.01 to 0.05 moles, based on 1 mole of the compound (2) or the compound (3). By setting the amount of a metallic compound used within the above described range, the metallic compound can be easily removed after completion of the reaction, and the reaction sufficiently progresses.

Preferred examples of the pro-oxidant used in the oxidation step of the present invention include: brominated substances such as sodium bromide, ammonium bromide or hydrogen bromide; and imide compounds such as N-hydroxyphthalimide, N-hydroxysuccinimide, trihydroxyisocyanuric acid, N-acetoxyphthalimide, and N-acetoxysuccinimide. Herein, the hydroxyl group of the imide compound may be protected. These pro-oxidants may be used singly or in combination of two or more types.

The above described pro-oxidant is used in an amount of preferably 0.001 to 1 mole, more preferably 0.01 to 0.5 moles, and particularly preferably 0.03 to 0.3 moles, based on 1 mole of the compound (2) or the compound (3). By setting the amount of a pro-oxidant used within the above described range, the pro-oxidant can be easily removed after completion of the reaction, or the reaction sufficiently progresses. Moreover, the corrosion of the reactor can also be avoided.

The type of molecular oxygen used in the oxidation step of the present invention is not particularly limited. Pure oxygen may be used, or oxygen diluted with inert gas such as nitrogen, argon, helium or carbon dioxide may also be used. From an economic standpoint, air is preferably used.

In the oxidation reaction of the present invention, molecular oxygen is used in an amount of preferably 2 moles or more, more preferably 3 to 10000 moles, and particularly preferably 6 to 1000 moles, based on 1 mole of the compound (2) or the compound (3). Using an excessive amount of molecular oxygen to the substrate (the compound (2) or the compound (3)), the reaction system can be prevented from becoming an anoxic condition, and side effects such as decarboxylation can be avoided.

The oxidation step of the present invention is preferably carried out in the presence of a solvent. The type of a solvent used is not particularly limited, as long as it does not inhibit the reaction. An example of such a solvent is lower aliphatic carboxylic acid. Preferably, aliphatic carboxylic acid having 1 to 4 carbon atoms, such as formic acid, acetic acid or propionic acid, is used. More preferably, formic acid and acetic acid are used. These solvents may be used singly or in combination of two or more types. The solvent may also be used in the form of an aqueous solution.

The above described solvent is used in an amount of preferably 1 to 100 g, more preferably 2 to 50 g, and further preferably 5 to 30 g, based on 1 g of the compound (2) or the compound (3).

In the oxidation step of the present invention, there is conducted, for example, a method which comprises mixing the compound (2) or the compound (3), a metallic compound, a pro-oxidant, and a solvent, and then allowing the compound (2) or the compound (3) to come into contact with molecular oxygen (e.g. air). Oxygen can be introduced into the reaction system by various methods such as continuous supply, sequential supply or batch supply. The reaction temperature applied during the reaction is preferably 20° C. to 170° C., and more preferably 80° C. to 150° C. The reaction pressure is preferably an ordinary pressure to 5 MPa, and more preferably 0.3 to 4 MPa.

By the oxidation step of the present invention, 3,4-dicarboalkoxybiphenyl-3',4'-dicarboxylic acid (including the corresponding acid anhydride) (the compound (1) or the compound (1-1)) can be obtained. After completion of the reaction, the obtained compound can be isolated and purified by a common method such as neutralization, extraction, filtration, concentration, distillation, recrystallization, crystallization or column chromatography.

The thus obtained 3,4-dicarboalkoxybiphenyl-3',4'-dicarboxylic acid (including the corresponding acid anhydride) can be induced to biphenyltetracarboxylic acid (s-BPTA) by further hydrolyzing it. Then, s-BPTA can be induced to a biphenyltetracarboxylic acid anhydride (s-BPDA) by dehydrating it.

EXAMPLES

Hereinafter, the present invention will be specifically described in the following examples. However, these examples are not intended to limit the scope of the present invention. It is to be noted that the analysis of reaction products was carried out by gas chromatography (FID detector, internal standard method).

Reference Example 1

Synthesis of Lanthanum-Deposited Zeolite
(Hereinafter Referred to as La/HY Catalyst)

2 g of lanthanum nitrate hexahydrate dissolved in 100 ml of ion exchange water was added at a room temperature to a suspension prepared by adding 5 g of H-type Y zeolite (manufactured by Tosoh Corporation; HSZ-320HOA) to 200 ml of ion exchange water. Then, the mixed solution was stirred at 90° C. for 3 hours. After completion of the stirring operation, a solid was separated from the reaction solution using a centrifuge, and it was then washed with 45 ml of ion exchange water five times, followed by drying at 85° C. overnight. After completion of the drying operation, the resultant was calcined under an air atmosphere at 500° C. for 2 hours. The obtained solid was analyzed with ICP (inductively-coupled plasma). As a result, the content of lanthanum atoms was found to be 5.6% by mass.

Reference Example 2

Synthesis of 3,4-dicarbomethoxycyclohexyl-3',4'-dimethylbenzene

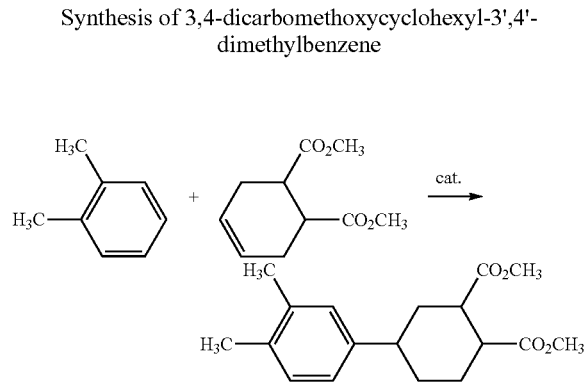

0.1 g of La/HY catalyst, 3 g (28.3 mmol) of orthoxylene, and 0.1 g (0.5 mmol) of cyclohexen-4,5-dicarboxylic acid methyl ester were added to an inner glass tube of an SUS-made autoclave equipped with a 50-ml inner glass tube. This autoclave was immersed in an oil bath that had previously been adjusted to 180° C., so that it could be reacted under a nitrogen atmosphere for 2 hours. After completion of the reaction, the reactor was cooled with water, the inner gas was released, and the reaction solution was then analyzed. As a result, it was found that 0.075 g of 3,4-dicarbomethoxycyclohexyl-3',4'-dimethylbenzene was generated (reaction yield relative to cyclohexen-4,5-dicarboxylic acid methyl ester: 50%).

Example 1

Synthesis of 3,4-dimethylbiphenyl-3',4'-dicarboxylic acid dimethyl ester (method A)

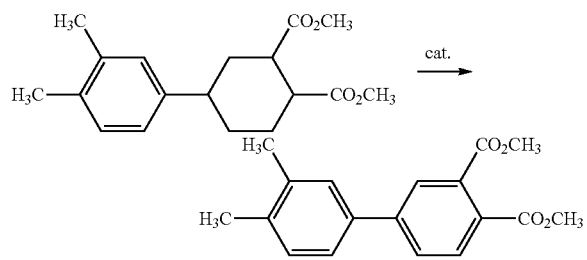

Orthoxylene was distilled away from the reaction solution obtained in Reference Example 2 using a rotary evaporator, and the resulting solution was then concentrated. Then, 0.03 g of 10-mass-% Pd/C (manufactured by Kishida Chemical Co., Ltd.) was added to the concentrate, and the obtained mixture was then reacted under a nitrogen atmosphere at 250° C. for 6 hours. After completion of the reaction, the reaction solution was analyzed. As a result, it was found that 0.03 g of 3,4-dimethylbiphenyl-3',4'-dicarboxylic acid dimethyl ester was generated (reaction yield: 20%).

Example 2-1

Synthesis of 3,4-dimethylbiphenyl-3',4'-dicarboxylic acid dimethyl ester (method (B))

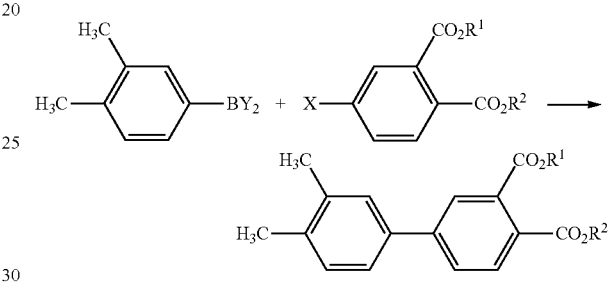

24.1 g (88 mmol) of dimethyl 4-bromophthalate, 14.5 g (97 mmol) of 3,4-dimethylphenylboronic acid, and 24.4 g (176 mmol) of potassium carbonate were added to a 500-mL three-necked round-bottom flask equipped with a stirrer, a thermometer and a reflux condenser tube, and the inside of the reaction system was maintained under an argon atmosphere. Subsequently, 270 mL of toluene, 30 mL of methanol, and 3.1 g (4.4 mmol) of dichlorobis(triphenylphosphine)palladium were added to the reaction system, and the obtained mixture was then reacted at 80° C. for 4 hours, while stirring.

After completion of the reaction, the reaction solution was cooled to a room temperature, and it was then filtrated with Celite. The filtrate was purified by silica gel column chromatography, and the obtained crude product was then dissolved in 100 mL of hot methanol to precipitate a crystal, to obtain 23.6 g of 3,4-dimethylbiphenyl-3',4'-dicarboxylic acid dimethyl ester in the form of a white solid (isolation yield: 90%).

The obtained 3,4-dimethylbiphenyl-3',4'-dicarboxylic acid dimethyl ester is a novel compound having the following physical properties.

Melting point: 92° C. to 94° C.

$^1$H-NMR (300 MHz, CDCl$_3$ (δ (ppm)); 2.31 (s, 3H), 2.33 (s, 3H), 3.92 (s, 3H), 3.94 (s, 3H), 7.20-7.39 (m, 3H), 7.70-7.88 (m, 3H)

$^{13}$C-NMR (75 MHz, CDCl$_3$ (δ (ppm)); 19.4, 19.8, 52.5, 52.6, 124.4, 126.9, 128.2, 128.9, 129.2, 129.6, 130.2, 133.0, 136.4, 137.1, 137.2, 144.3, 167.5, 168.4

IR (KBr, cm$^{-1}$); 3448, 3073, 3030, 2984, 2946, 2914, 2860, 1739, 1714

Elemental analysis: 72.36% carbon; 5.97% hydrogen (Theoretical value (C$_{18}$H$_{18}$O$_4$): 72.47% carbon; 6.08% hydrogen)

Example 2-2

$R^1=R^2=R^3=R^4$=methyl group; synthesis of 3,4-dimethyl-biphenyl-3',4'-dicarboxylic acid dimethyl ester 24.1 g (88 mmol) of dimethyl 4-bromophthalate, 14.5 g (97 mmol) of 3,4-dimethylphenylboronic acid, and 24.4 g (176 mmol) of potassium carbonate were added to a 500-mL three-necked round-bottom flask equipped with a stirrer, a thermometer and a reflux condenser, and the inside of the reaction system was maintained under an argon atmosphere. Subsequently, 270 mL of toluene, 30 mL of methanol, and 3.1 g (4.4 mmol) of dichlorobis(triphenylphosphine)palladium were added to the reaction system, and the obtained mixture was then reacted at 80° C. for 4 hours, while stirring.

After completion of the reaction, the reaction solution was cooled to a room temperature, and it was then filtrated with Celite. The filtrate was purified by silica gel column chromatography and was then concentrated.

The obtained concentrate was recrystallized using 100 mL of hot methanol, to obtain 23.6 g of 3,4-dimethyl-biphenyl-3',4'-dicarboxylic acid dimethyl ester in the form of a white solid (isolation yield: 90%).

The obtained 3,4-dimethyl-biphenyl-3',4'-dicarboxylic acid dimethyl ester had the following physical properties.

Melting point: 92° C. to 94° C.

$^1$H-NMR (CDCl$_3$, δ (ppm)): 2.31 (s, 3H), 2.33 (s, 3H), 3.92 (s, 3H), 3.94 (s, 3H), 7.20-7.39 (m, 3H), 7.70-7.88 (m, 3H)

$^{13}$C-NMR (CDCl$_3$, δ (ppm)): 19.4, 19.8, 52.5, 52.6, 124.4, 126.9, 128.2, 128.9, 129.2, 129.6, 130.2, 133.0, 136.4, 137.1, 137.2, 144.3, 167.5, 168.4

IR (KBr, cm$^{-1}$): 3448, 3073, 3030, 2984, 2946, 2914, 2860, 1739, 1714.

Elemental analysis (C$_{18}$H$_{18}$O$_4$): 72.47% carbon; 5.77% hydrogen (Calculated value: 72.47% carbon; 6.08% hydrogen)

Example 3-1

Synthesis of 3,4-dicarbomethoxybiphenyl-3',4'-dicarboxylic acid

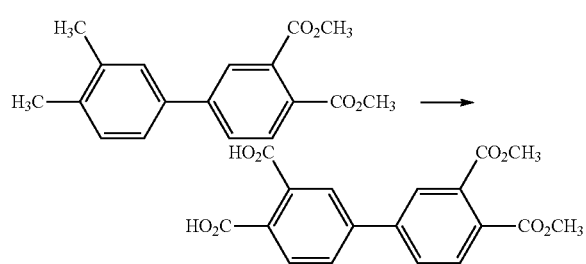

The 3,4-dimethylbiphenyl-3',4'-dicarboxylic acid dimethyl ester obtained by the same method as that described in Example 2-1, cobalt acetate tetrahydrate, manganese acetate tetrahydrate, N-hydroxyphthalimide, and acetic acid were mixed, and the obtained mixture was then reacted under an air atmosphere (3 Mpa) at 150° C. for 5 hours, while stirring. After completion of the reaction, the obtained reaction solution was analyzed. As a result, it was found that 3,4-dicarbomethoxy-biphenyl-3',4'-dicarboxylic acid was obtained at a reaction yield of 99%.

Example 3-2

$R^1=R^2$=methyl group, n=0; synthesis of 3,4-dicarbomethoxybiphenyl-3',4'-dicarboxylic acid and 3,4-dicarbomethoxybiphenyl-3',4'-dicarboxylic acid anhydride

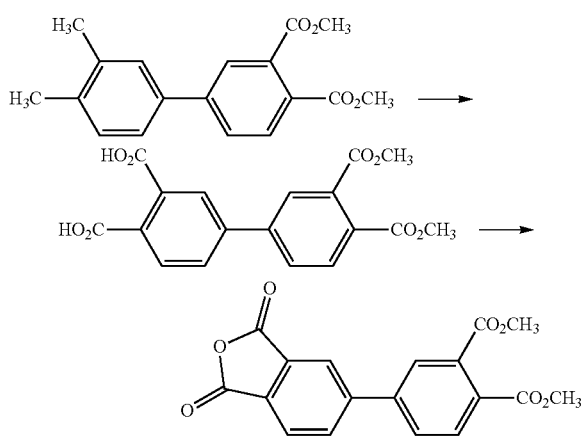

2.98 g (10 mmol) of 3,4-dimethyl-biphenyl-3',4'-dicarboxylic acid dimethyl ester, 12.4 mg (0.05 mmol) of cobalt acetate tetrahydrate, 12.2 mg (0.05 mmol) of manganese acetate tetrahydrate, 163 mg (1.0 mmol) of N-hydroxyphthalimide (hereinafter referred to as NHPI), and 15 ml of acetic acid were added to a titanium-made autoclave with an internal volume of 100 mL, and the reaction was initiated under an air atmosphere (internal pressure: 3 Mpa) at 150° C. One hour after initiation of the reaction, the reactor was cooled to a room temperature, and the inner gas was released. Thereafter, NHPI was added in the same amount as described above to the autoclave, and the reaction was initiated again at 150° C. One hour later, this series of operations (cooling-depressurization-addition-repressurization, and heating and stirring) were repeated, and thus, the reaction was carried out for a total of 3 hours.

After completion of the reaction, the reactor was cooled to a room temperature, and the inner gas was released. The solvent was distilled away from the obtained reaction solution, and ethyl acetate and water were then added to the residue, followed by liquid separation. Thereafter, an ethyl acetate layer was washed with water to remove the metallic compounds.

The obtained organic layer was analyzed by liquid chromatography. As a result, it was found that 3,4-dicarbomethoxybiphenyl-3',4'-dicarboxylic acid was generated (reaction yield: 93%).

Thereafter, the organic layer was concentrated, and the concentrate was then distilled away under a reduced pressure, to obtain 2.37 g of 3,4-dicarbomethoxybiphenyl-3',4'-dicarboxylic acid anhydride in the form of a white solid (isolation yield: 70%).

The obtained 3,4-dicarbomethoxybiphenyl-3',4'-dicarboxylic acid anhydride is a novel compound having the following physical properties.

Melting point: 200° C. to 202° C.

$^1$H-NMR (CDCl$_3$, δ (ppm)): 3.94 (s, 3H), 3.95 (s, 3H), 7.79-8.22 (m, 6H)

$^{13}$C-NMR (CDCl$_3$, δ (ppm)): 52.8, 53.0, 124.1, 126.4, 127.9, 129.8, 130.1, 130.5, 132.4, 132.5, 133.2, 134.8, 140.8, 147.3, 162.2, 162.4, 167.2, 167.3

IR (microscopic ATR technique, cm$^{-1}$): 2958, 1856, 1832, 1813, 1773, 1732, 1719

Elemental analysis (C$_{18}$H$_{12}$O$_7$): 63.36% carbon; 3.35% hydrogen (Calculated value: 63.53% carbon; 3.55% hydrogen)

Example 4

R$^1$=R$^2$=methyl group, n=1; synthesis of 3,4-dicarbomethoxybiphenyl-3',4'-dicarboxylic acid monohydrate

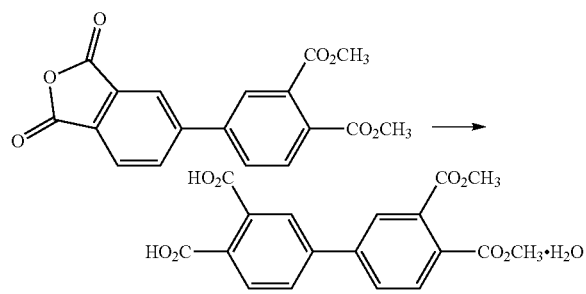

5.10 g (15 mmol) of the 3,4-dicarbomethoxybiphenyl-3',4'-dicarboxylic acid anhydride synthesized by the same method as that described in Example 3-2 and 30 ml of water were added to an eggplant flask with an internal volume of 100 ml, equipped with a condenser tube, and the obtained mixture was then reacted at 100° C. for 2 hours, while stirring.

After completion of the reaction, the reaction solution was cooled to a room temperature. Thereafter, the precipitated solid was filtrated and was then washed with water. The obtained solid was dried, to obtain 5.62 g of the 3,4-dicarbomethoxybiphenyl-3',4'-dicarboxylic acid monohydrate in the form of a white solid (isolation yield: 99%).

The 3,4-dicarbomethoxybiphenyl-3',4'-dicarboxylic acid monohydrate is a novel compound having the following physical properties.

Melting point: 114° C. to 116° C.

$^1$H-NMR (acetone-d$_6$, δ (ppm)): 3.899 (s, 3H), 3.903 (s, 3H), 7.89-8.13 (m, 6H)

$^{13}$C-NMR (acetone-d$_6$, δ (ppm)): 52.9, 53.0, 128.2, 128.3, 130.2, 130.5, 130.7, 130.8, 132.3, 133.1, 134.3, 134.9, 142.3, 142.8, 167.9, 168.2, 168.3, 168.6

IR (microscopic ATR technique, cm$^{-1}$): 3535, 3414, 3163, 2955, 2638, 2510, 1731, 1709, 1669, 1633

Elemental analysis (C$_{18}$H$_{14}$O$_8$·H$_2$O): 57.42% carbon; 4.10% hydrogen (Calculated value: 57.45% carbon; 4.29% hydrogen)

Example 5

R$^1$=R$^2$=methyl group, n=1; synthesis of 3,4-dicarbomethoxybiphenyl-3',4'-dicarboxylic acid monohydrate

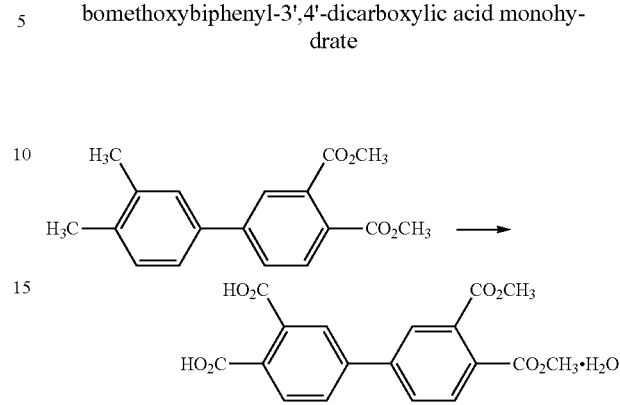

2.98 g (10 mmol) of the 3,4-dimethyl-biphenyl-3',4'-dicarboxylic acid dimethyl ester, 12.4 mg (0.05 mmol) of cobalt acetate tetrahydrate, 12.2 mg (0.05 mmol) of manganese acetate tetrahydrate, 163 mg (1.0 mmol) of N-hydroxyphthalimide (hereinafter referred to as NHPI), and 15 ml of acetic acid were added to a titanium-made autoclave with an internal volume of 100 mL, and the reaction was initiated under an air atmosphere (internal pressure: 3 Mpa) at 150° C. One hour after initiation of the reaction, the reactor was cooled to a room temperature, and the inner gas was released. Thereafter, NHPI was added in the same amount as described above to the autoclave, and the reaction was initiated again at 150° C. One hour later, this series of operations (cooling-depressurization-addition-repressurization, and heating and stirring) were repeated, and thus, the reaction was carried out for a total of 3 hours.

After completion of the reaction, the reaction solution was cooled to a room temperature. The precipitated solid was filtrated and was then washed with methanol/water. The obtained filtrate was dried, to obtain 2.82 g of 3,4-dicarbomethoxybiphenyl-3',4'-dicarboxylic acid monohydrate (isolation yield: 75%).

Example 6

Synthesis of 3,4,3',4'-biphenyltetracarboxylic acid anhydride

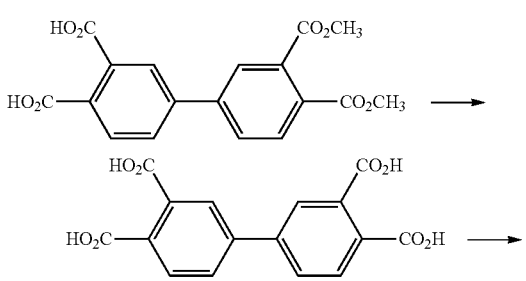

-continued

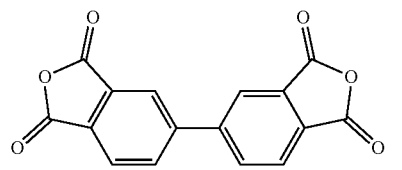

The 3,4-dicarbomethoxy-biphenyl-3',4'-dicarboxylic acid obtained in Example 3-1 was reacted with concentrated hydrochloric acid to obtain 3,4,3',4'-biphenyltetracarboxylic acid (s-BPTA). Then, the obtained 3,4,3',4'-biphenyltetracarboxylic acid was reacted in acetic anhydride under heating, to obtain a 3,4,3',4'-biphenyltetracarboxylic acid anhydride (s-BPDA).

What is claimed is:

1. A method for producing a 3,4-dialkylbiphenyl-3',4'-dicarboxylic acid compound represented by a general formula (2), the method comprising subjecting a 3,4-dicarboalkoxycyclohexyl-3',4'-alkylbenzene compound represented by a general formula (4-1) to a dehydrogenation reaction in the presence of a metallic catalyst;

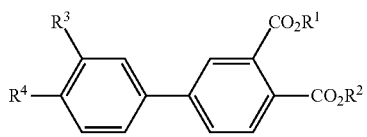
(2)

wherein $R^1$ and $R^2$ each represents a hydrogen atom or an alkyl group having 1 to 4 carbon atoms, and $R^3$ and $R^4$ each represents an alkyl group having 1 to 4 carbon atoms;

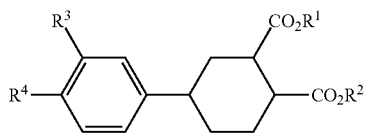
(4-1)

wherein $R^1$, $R^2$, $R^3$, and $R^4$ have the same definitions as those described above.

2. The method for producing a 3,4-dialkylbiphenyl-3',4'-dicarboxylic acid compound according to claim 1, wherein the 3,4-dialkylbiphenyl-3',4'-dicarboxylic acid compound is represented by a general formula (3):

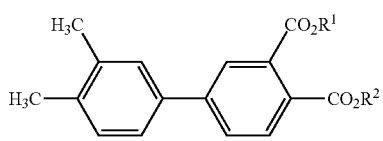
(3)

wherein $R^1$ and $R^2$ each represents a hydrogen atom or an alkyl group having 1 to 4 carbon atoms, and
the 3,4-dicarboalkoxycyclohexyl-3',4'-alkylbenzene compound is represented by a general formula (4-2):

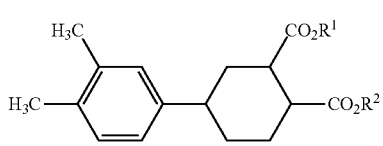
(4-2)

wherein $R^1$ and $R^2$ have the same definitions as those described above.

* * * * *